US010650405B2

(12) United States Patent
Hoffman et al.

(10) Patent No.: US 10,650,405 B2
(45) Date of Patent: May 12, 2020

(54) MEDIA CONTENT TRACKING

(71) Applicant: Kellogg Company, Battle Creek, MI (US)

(72) Inventors: Gustav Hoffman, Richland, MI (US); Ganapa Sashidhara Murthy, Portage, MI (US)

(73) Assignee: Kellogg Company, Battle Creek, MI (US)

( * ) Notice: Subject to any disclaimer, the term of this patent is extended or adjusted under 35 U.S.C. 154(b) by 193 days.

(21) Appl. No.: 15/465,022

(22) Filed: Mar. 21, 2017

(65) Prior Publication Data

US 2018/0276706 A1    Sep. 27, 2018

(51) Int. Cl.
*G09G 5/00*    (2006.01)
*G06Q 30/02*    (2012.01)
(Continued)

(52) U.S. Cl.
CPC ....... *G06Q 30/0246* (2013.01); *A61B 5/0077* (2013.01); *A61B 5/1114* (2013.01);
(Continued)

(58) Field of Classification Search
None
See application file for complete search history.

(56) References Cited

U.S. PATENT DOCUMENTS 9,285,874 B2    3/2016 Bychkov et al.
2008/0278289 A1*  11/2008 Gantner ............. G06K 7/10079
                                              340/10.1
(Continued)

FOREIGN PATENT DOCUMENTS

JP    2012047945 A  *  3/2012
JP    2012047945 A  *  3/2012
(Continued)

OTHER PUBLICATIONS

Merriam-Webster Online dictionary, https://www.merriam-webster.com/dictionary/genre, 2019, p. 2 (Year: 2019).*
(Continued)

*Primary Examiner* — Priyank J Shah
*Assistant Examiner* — Kirk W Hermann
(74) *Attorney, Agent, or Firm* — Honigman LLP

(57) ABSTRACT

A method for media content tracking is disclosed. The method includes receiving a user identifier and instructing display systems to display media content based on the user identifier. Each display system has a corresponding screen. The method also includes receiving image data from an imaging system configured to have a field of view arranged to capture images of a user. The method further includes determining gaze characteristics of the user including a gaze target of the user. The method further includes determining whether the gaze target corresponds to one of the screens. When the gaze target corresponds to one of the screens, the method includes determining a time period of gaze engagement with the corresponding screen. The method also includes storing at least one of the gaze characteristics and the media content or an identifier of the media content displayed on the screen corresponding to the gaze target.

30 Claims, 10 Drawing Sheets

(51) Int. Cl.
| | |
|---|---|
| *G06K 9/00* | (2006.01) |
| *G06F 3/14* | (2006.01) |
| *H04N 21/414* | (2011.01) |
| *H04N 21/441* | (2011.01) |
| *H04N 21/45* | (2011.01) |
| *A61B 5/00* | (2006.01) |
| *H04N 21/4223* | (2011.01) |
| *G06F 3/03* | (2006.01) |
| *H04N 21/442* | (2011.01) |
| *G06F 3/01* | (2006.01) |
| *A61B 5/11* | (2006.01) |
| *A61B 5/16* | (2006.01) |

(52) U.S. Cl.
CPC ............ *A61B 5/163* (2017.08); *A61B 5/7264* (2013.01); *G06F 3/013* (2013.01); *G06F 3/0304* (2013.01); *G06F 3/1446* (2013.01); *G06K 9/0061* (2013.01); *G06K 9/00268* (2013.01); *G06K 9/00604* (2013.01); *G06Q 30/02* (2013.01); *H04N 21/41415* (2013.01); *H04N 21/4223* (2013.01); *H04N 21/441* (2013.01); *H04N 21/44204* (2013.01); *H04N 21/44218* (2013.01); *H04N 21/44222* (2013.01); *H04N 21/4532* (2013.01); *A61B 2503/12* (2013.01); *A61B 2576/00* (2013.01)

(56) References Cited

U.S. PATENT DOCUMENTS

| | | | |
|---|---|---|---|
| 2009/0322678 A1* | 12/2009 | Lashina | G06Q 30/02 |
| | | | 345/158 |
| 2010/0191631 A1 | 7/2010 | Weidmann | |
| 2010/0295774 A1 | 11/2010 | Hennessey | |
| 2010/0313214 A1* | 12/2010 | Moriya | G06K 9/00771 |
| | | | 725/12 |
| 2012/0265616 A1* | 10/2012 | Cao | G06Q 30/0261 |
| | | | 705/14.58 |
| 2013/0205232 A1* | 8/2013 | Vandermolen | G06F 3/0481 |
| | | | 715/760 |
| 2013/0307771 A1* | 11/2013 | Parker | G06F 3/013 |
| | | | 345/158 |
| 2014/0316543 A1 | 10/2014 | Sharma et al. | |
| 2015/0106386 A1* | 4/2015 | Lee | G06F 16/95 |
| | | | 707/748 |
| 2016/0292720 A1 | 10/2016 | Wooden | |
| 2016/0370584 A1 | 12/2016 | Teller | |
| 2017/0109513 A1* | 4/2017 | Skogo | G06F 21/32 |
| 2017/0139475 A1* | 5/2017 | Eivazi | G06F 3/013 |
| 2017/0212583 A1* | 7/2017 | Krasadakis | G06F 3/013 |
| 2018/0211285 A1* | 7/2018 | Todasco | G06Q 30/0269 |

FOREIGN PATENT DOCUMENTS

| | | | | |
|---|---|---|---|---|
| JP | | 05325181 B2 | 10/2013 | |
| WO | | 2014100280 A1 | 6/2014 | |
| WO | | 2015060936 A1 | 4/2015 | |
| WO | WO 2016112531 A1 * | | 7/2016 | ............ G06F 3/013 |
| WO | WO-2016112531 A1 * | | 7/2016 | ............ G06F 3/013 |

OTHER PUBLICATIONS

International Preliminary Report on Patentability, PCT/US2018/022676, dated Oct. 3, 2019, 12 pages.

Florian S. Alt, "A design space for pervasive advertising on public displays," Mar. 12, 2013, 390 pages.

* cited by examiner

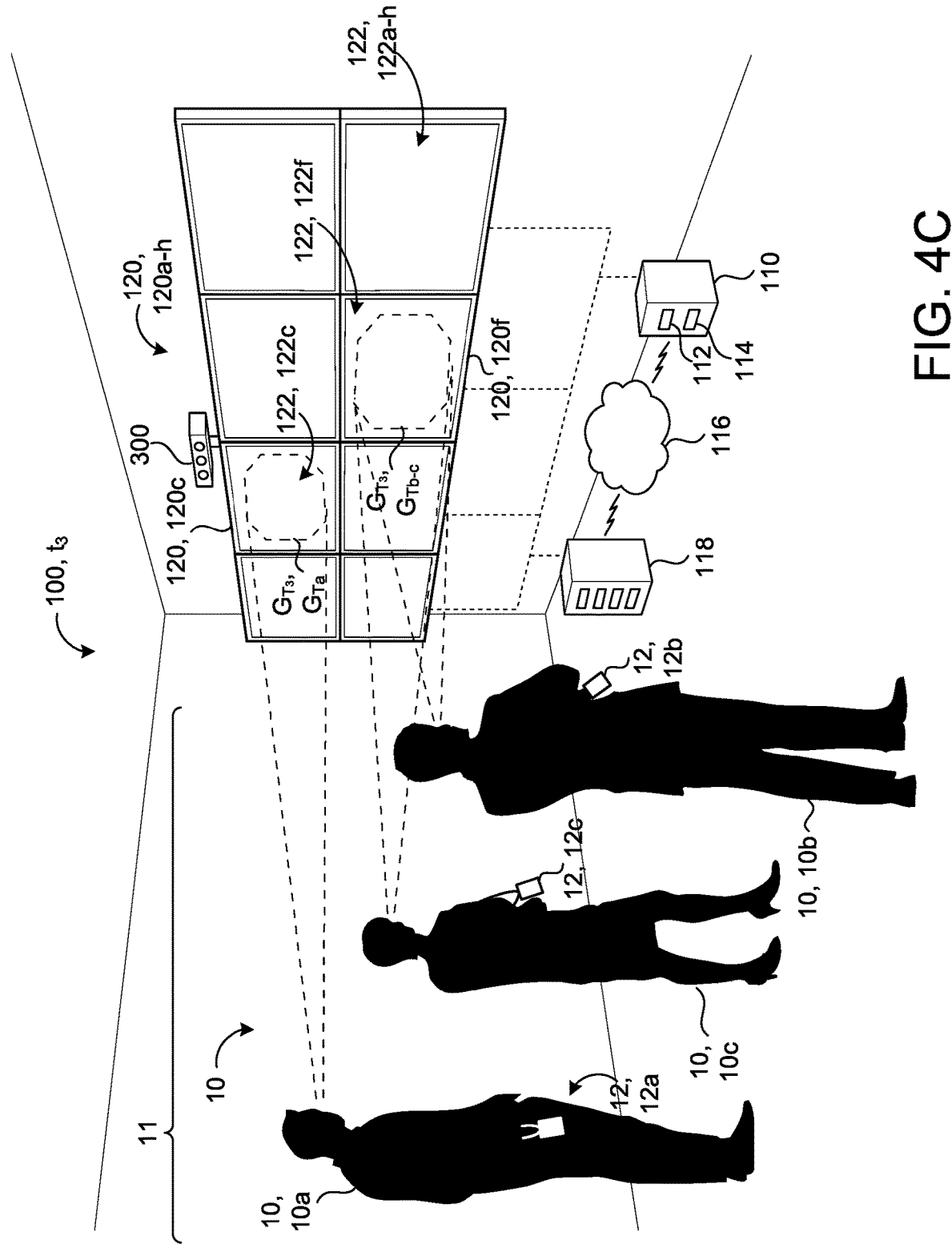

MEDIA CONTENT TRACKING

TECHNICAL FIELD

This disclosure relates to tracking audience engagement of various media content.

BACKGROUND

Society often measures the success of media content by an ability of the media content to capture the attention of a person or an audience. For example, movies are measured by box office attendance. Books are measured by copies sold. The internet values social media by likes and by comments and, generally, digital advertising is tracked according to clicks and according to activity responses. For these reasons, some companies consider the era today as the advertising era and spend billions of dollars to advertise and to understand the captivating nature of media content. While known systems and methods of media content tracking have proven acceptable for their intended purpose, a continuous need for improvement in the relevant art remains.

SUMMARY

One aspect of the disclosure provides a method for media content tracking. The method includes receiving, at data processing hardware, a user identifier associated with a user and instructing, by the data processing hardware, display systems to display media content based on the user identifier. Each display system has a corresponding screen. The method also includes receiving, at the data processing hardware, image data from an imaging system configured to have a field of view arranged to capture images of the user. The method further includes determining, by the data processing hardware, gaze characteristics of the user based on the image data. The gaze characteristics include a gaze target of the user. The method further includes determining, by the data processing hardware, whether the gaze target corresponds to one of the screens. When the gaze target corresponds to one of the screens, the method includes determining, by the data processing hardware, a time period of gaze engagement with the corresponding screen based on the gaze characteristics of the user. The method also includes storing, by the data processing hardware, in memory hardware: at least one of the gaze characteristics of the user or the time period of gaze engagement with the corresponding screen; and the media content or an identifier of the media content displayed on the screen corresponding to the gaze target.

Implementations of the disclosure may include one or more of the following optional features. In some implementations, when the gaze target corresponds to one of the screens, the method includes instructing, by the data processing hardware, the display system of another one of the screens away from the gaze target to display the media content displayed on the screen corresponding to the gaze target and determining, by the data processing hardware, whether the gaze characteristics of the user indicate a change in the gaze target to the another one of the screens. Determining the gaze characteristics of the user may include determining a gaze direction of the user and the gaze target of the user based on the gaze direction of the user. Instructing the display systems to display media content may include instructing each display system to display a genre of media content for an interval of time. At least two display systems display different genres of media content at the same interval of time.

In some implementations, the method includes determining, by the data processing hardware, a collective time period of gaze engagement by the user in a genre of media content based on any time periods of gaze engagement of the user with the corresponding genre of media content. The method may also include identifying, by the data processing hardware, any genres of media content having received at least one of: (i) a threshold time number of gazes by the user; or (ii) a threshold a collective time period of gaze engagement by the user. The method may further include determining, by the data processing hardware, the user identifier based on the image data. The method also includes identifying, by the data processing hardware, facial features of the user identifier based on the image data and determining, by the data processing hardware, the user identifier based on the facial features of the user.

The imaging system may include at least one of: a camera; a three-dimension volumetric point cloud imaging sensor; stereo cameras; a light detection and ranging (LIDAR) system; or a laser detection and ranging (LADAR) system. Receiving the user identifier may include receiving a near-field measurement from an electro-magnetic near-field scanner.

Another aspect of the disclosure provides a method for media content tracking. The method includes receiving, at data processing hardware, user identifiers associated with a plurality of users and instructing, by the data processing hardware, display systems to display media content based on the user identifiers, the display system having a corresponding screen. The method also includes receiving, at the data processing hardware, image data from an imaging system configured to have a field of view arranged to capture images of the users and determining, by the data processing hardware, gaze characteristics of the users based on the image data. The gaze characteristics include a respective gaze target of each user. For each user, the method includes determining, by the data processing hardware, whether the respective gaze target of the user corresponds to one of the screens. When the respective gaze target of the user corresponds to one of the screens, the method includes determining, by the data processing hardware, a time period of gaze engagement with the corresponding screen based on the respective gaze target of the user and associating, by the data processing hardware, the time period of gaze engagement with the media content displayed on the corresponding screen. The method further includes identifying, by the data processing hardware, genres of media content receiving gaze engagement by the users based on the associations of the time periods of gaze engagement of the users with the corresponding media content and storing, by the data processing hardware, the identified genres of media content in memory hardware.

This aspect may include one or more of the following optional features. In some implementations, the method includes storing, by the data processing hardware, in memory hardware, for each user when the respective gaze target of the user corresponds to one of the screens: at least one of the gaze characteristics of the user or the respective time period of gaze engagement of the user; and the media content or an identifier of the media content displayed on the screen corresponding to the gaze target. Instructing the display systems to display media content may include instructing each display system to display a genre of media content for an interval of time, at least two display systems displaying different genres of media content at the same interval of time. The method may also include determining, by the data processing hardware, a threshold concentration of collective gaze engagement by the users in a genre of media content based on the associations of the time periods of gaze engagement of the users with the corresponding media content.

In some examples, the method includes identifying, by the data processing hardware, any genres of media content having received at least one of: a threshold time number of gazes by the users; a threshold time period of gaze engagement by one or more of the users; or a threshold concentration of collective gaze engagement by the users. The method may also include determining, by the data processing hardware, the user identifier based on the image data. The method may further include identifying, by the data processing hardware, facial features of the user identifier based on the image data and determining, by the data processing hardware, the user identifier based on the facial features of the user.

The imaging system may include at least one of: a camera; a three-dimension volumetric point cloud imaging sensor; stereo cameras; a light detection and ranging (LIDAR) system; or a laser detection and ranging (LADAR) system. Receiving the user identifier may include receiving a near-field measurement from an electro-magnetic near-field scanner.

Yet another aspect of the disclosure provides a system for media content tracking. The system includes data processing hardware in communication with the collection of displays and memory hardware in communication with the data processing hardware. The memory hardware stores instructions that when executed on the data processing hardware cause the data processing hardware to perform operations. The operations include receiving a user identifier associated with a user, instructing display systems to display media content based on the user identifier, each display system having a corresponding screen, and receiving image data from an imaging system configured to have a field of view arranged to capture images of the user. The operations also include determining gaze characteristics of the user based on the image data, the gaze characteristics comprising a gaze target of the user, and determining whether the gaze target corresponds to one of the screens. When the gaze target corresponds to one of the screens, the operations include determining a time period of gaze engagement with the corresponding screen based on the gaze characteristics of the user. The operations further include storing in the memory hardware at least one of the gaze characteristics of the user or the time period of gaze engagement with the corresponding screen and the media content or an identifier of the media content displayed on the screen corresponding to the gaze target.

This aspect may include one or more of the following optional features. In some implementations, the operations include when the gaze target corresponds to one of the screens instructing the display system of another one of the screens away from the gaze target to display the media content displayed on the screen corresponding to the gaze target and determining whether the gaze characteristics of the user indicate a change in the gaze target to the another one of the screens. Determining the gaze characteristics of the user may include determining a gaze direction of the user and the gaze target of the user based on the gaze direction of the user.

In some examples, instructing the display systems to display media content includes instructing each display system to display a genre of media content for an interval of time, at least two display systems displaying different genres of media content at the same interval of time. The operations may also include determining a collective time period of gaze engagement by the user in a genre of media content based on any time periods of gaze engagement of the user with the corresponding genre of media content. The operations may further include identifying any genres of media content having received at least one of a threshold time number of gazes by the user or a threshold a collective time period of gaze engagement by the user. The operations may also include determining the user identifier based on the image data.

In some implementations, the operations include identifying facial features of the user identifier based on the image data and determining the user identifier based on the facial features of the user. The imaging system may include at least one of: a camera; a three-dimension volumetric point cloud imaging sensor; stereo cameras; a light detection and ranging (LIDAR) system; or a laser detection and ranging (LADAR) system. The operation of receiving the user identifier may include receiving a near-field measurement from an electro-magnetic near-field scanner.

Yet another aspect of the disclosure provides a system for media content tracking. The system includes data processing hardware in communication with the collection of displays and memory hardware in communication with the data processing hardware. The memory hardware stores instructions that when executed on the data processing hardware cause the data processing hardware to perform operations. The operations include receiving user identifiers associated with a plurality of users and instructing display systems to display media content based on the user identifiers, the display system having a corresponding screen. The operations also include receiving image data from an imaging system configured to have a field of view arranged to capture images of the users and determining gaze characteristics of the users based on the image data, the gaze characteristics comprising a respective gaze target of each user. For each user, the operations include determining whether the respective gaze target of the user corresponds to one of the screens. When the respective gaze target of the user corresponds to one of the screens, the operations include determining a time period of gaze engagement with the corresponding screen based on the respective gaze target of the user and associating the time period of gaze engagement with the media content displayed on the corresponding screen. The operations further include identifying genres of media content receiving gaze engagement by the users based on the associations of the time periods of gaze engagement of the users with the corresponding media content and storing the identified genres of media content in memory hardware.

This aspect may include one or more of the following optional features. In some implementations, the operations include storing in memory hardware, for each user when the respective gaze target of the user corresponds to one of the screens, at least one of the gaze characteristics of the user or the respective time period of gaze engagement of the user, and the media content or an identifier of the media content displayed on the screen corresponding to the gaze target. Instructing the display systems to display media content may include instructing each display system to display a genre of media content for an interval of time. At least two display systems may display different genres of media content at the same interval of time. The operations may further include determining a threshold concentration of collective gaze engagement by the users in a genre of media content based on the associations of the time periods of gaze engagement of the users with the corresponding media content.

In some implementations, the operations include identifying any genres of media content having received at least one of: a threshold time number of gazes by the users; a threshold time period of gaze engagement by one or more of the users; or a threshold concentration of collective gaze engagement by the users. The operations may also include determining the user identifier based on the image data. In some examples, the operations include identifying facial features of the user identifier based on the image data and determining the user identifier based on the facial features of the user.

The imaging system may include at least one of: a camera; a three-dimension volumetric point cloud imaging sensor; stereo cameras; a light detection and ranging (LIDAR) system; or a laser detection and ranging (LADAR) system. Receiving the user identifier may include receiving a near-field measurement from an electro-magnetic near-field scanner.

The details of one or more implementations of the disclosure are set forth in the accompanying drawings and the description below. Other aspects, features, and advantages will be apparent from the description and drawings, and from the claims.

DESCRIPTION OF DRAWINGS

FIG. 4C is a schematic view of the media content tracking environment at a third interval of time.

Like reference symbols in the various drawings indicate like elements.

DETAILED DESCRIPTION

As companies invest money and time into goods and services, the companies may use tools to determine ways to attract attention from consumers to their goods and their services. Companies have, therefore, traditionally studied consumer habits and consumer behaviors with focus groups and surveys as a means of consumer research to receive feedback and opinions of consumers. These traditional methods, however, often suffer from inherent biases such poor question design or researcher bias. Consumers may also skew their responses to place themselves in a favorable public light. With these traditional means, consumer research struggles to capture organic consumer habits and consumer behaviors. A media content tracking environment enables a company to conduct consumer research related to media content while reducing traditional biases. In the media content tracking environment, a consumer or a user participates in a viewing session over a period of time. During the viewing session, the media content tracking environment feeds the user media content while observing, collecting and storing image data regarding interactions of the user with the media content.

Figure 1A:
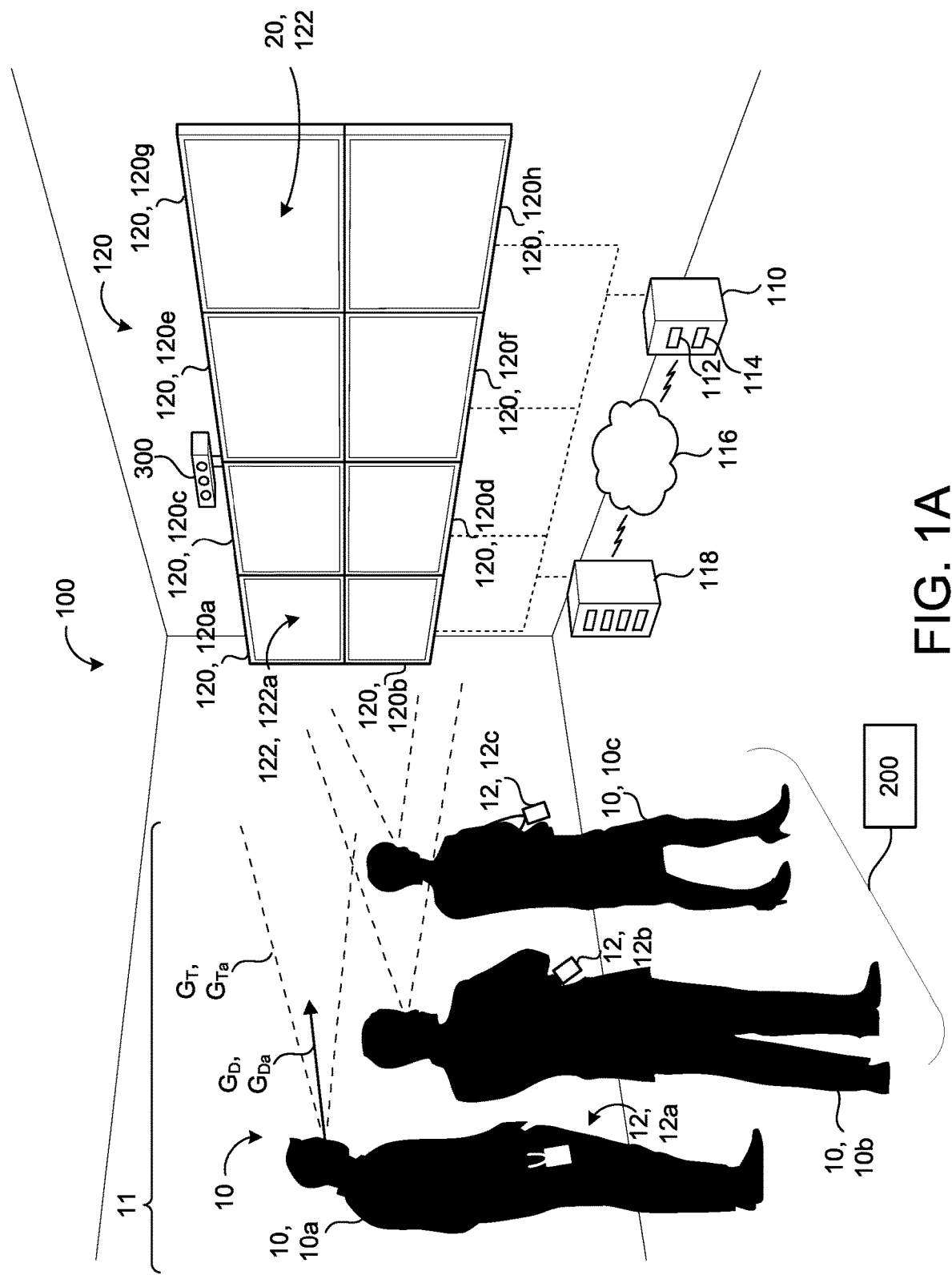
FIG. 1A is a schematic view of an example media content tracking environment.
Figure 1B:
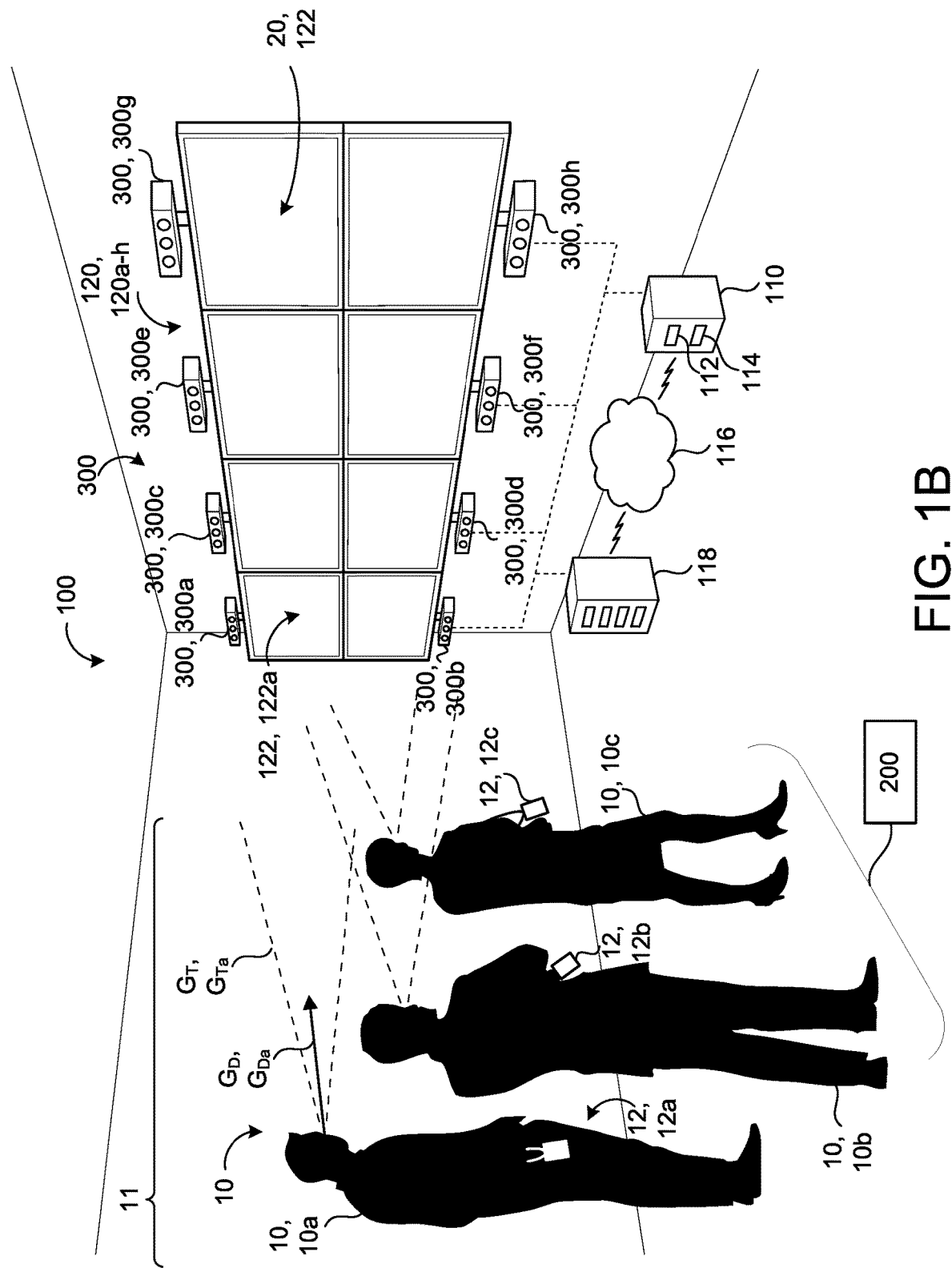
FIG. 1B is a schematic view of another example media content tracking environment.

FIGS. 1A and 1B illustrate at least one user 10 participating in an example media content tracking environment 100. The media content tracking environment 100 includes a processing system 110, an identification system 200, and an imaging system 300. The at least one user 10 of the media content tracking environment 100 may be n number of users. Each user 10, 10a-n has a user identifier 12, 12a-n. (In the figures only three users 10a-c are shown for example purposes only). The identification system 200 receives the user identifier 12 of the corresponding user 10 and communicates the user identifier 12 to the processing system 110. In some examples, the user 10 actively communicates his/her user identifier 12 to the identification system 200, for example, by entering the user identifier 12 on a user interface (e.g., keyboard, touch screen, etc.), scanning a badge or card at card reader, placing his/her face in view of a facial recognition system, etc. In other examples, the user 10 passively communicates his/her user identifier 12 to the identification system 200, for example, by possessing a radio frequency (RF) identifier card, which is read passively by an RF reader, by facial recognition of a facial recognition system configured to identify and capture facial features of any users 10, 10a-n within the media content tracking environment 100, etc. Other ways of identifying the user 10 are possible as well.

Based on the user identifier 12, the processing system 110 is configured to display media content 20 to the user 10 by display systems 120. Each display system 120, 120a-n of the display systems 120 has a corresponding screen 122 depicting media content 20. Some examples of the display systems 120 include televisions, monitors, or projector and screen combinations.

Each user 10, 10a-n has gaze characteristics that the imaging system 300 identifies to determine whether the user 10 has an interest in the depicted media content 20. The gaze characteristics include a gaze target $G_T$ that corresponds to a subject of focus (i.e., a center of interest) within a field of view $F_V$ of the user 10. For example, referring to FIGS. 1A and 1B, the display systems 120 are in a field of view $F_V$ of a first user 10, 10a, but a gaze target $G_T$, $G_{Ta}$ of the first user 10, 10a is media content 20 displayed on a first screen 122, 122a. In some implementations, gaze characteristics also include a gaze direction $G_D$ of the user 10. The gaze direction $G_D$ of the user 10 may assist the processing system 110 to determine the gaze target $G_T$ of the user 10. For example, the processing system 110 determines the gaze direction $G_D$ from at least one image 310 captured by the imaging system 300. In some examples, the gaze direction $G_D$ is a vector determined by the processing system 110. The processing system 110 may determine the vector of the gaze direction $G_D$ according to at least one facial feature 14 of the user 10. The at least one facial feature 14 of the user 10 may be at least one eye E, a nose, a mouth, an ear, or any facial feature 14 whose position may permit the processing system 110 to determine the gaze direction $G_D$. The processing system 110 may also determine the vector of the gaze direction $G_D$ according to a posture P of the user 10, such as shoulder alignment, head tilt, or head alignment. With parameters, such as the gaze direction $G_D$ and an input of display screen locations, the processing system 110 may determine the display screen 122 of interest corresponding to the gaze target $G_T$ of the user 10 by approximating an intersection point of the vector of the gaze direction $G_D$ and a plane corresponding to the display screens 122 of the display systems 120.

With continued reference to FIGS. 1A and 1B, the processing system 110 of the media content tracking environment 100 includes data processing hardware 112 and memory hardware 114. In some implementations, the data processing hardware 112 and/or the memory hardware 114 are in communication with a network 116 associated with a server 118. In some implementations, the data processing hardware 112 receives the user identifier 12 associated with the user 10, instructs the display systems 120 to display media content 20 (e.g., based on the user identifier 12), and determines whether the gaze target $G_T$ of the user 10 corresponds to one of the display screens 122, 112a-h of the display systems 120. When the gaze target $G_T$ corresponds to one of the display screens 122, 112a-h of the display systems 120, the data processing hardware 112 stores within the memory hardware 114 gaze characteristics of the user 10 and optionally the related media content 20 subject of the gaze target $G_T$ or a media content characteristic (e.g., a media content identifier 22, an association 24 related to the media content 20, or a genre 26 of the media content 20) subject of the gaze target $G_T$. For example, the media content identifier 22 may be a tag of information including at least one media content characteristic, such as a media content provider, a media content genre, a media content target audience, or other custom media content identifications. Similarly, an association 24 related to the media content 20 may be a date code or a session code that relates to the media content 20 provided within the media content tracking environment 100. Additionally or alternatively, the processing system 110 may determine some of the gaze characteristics of the user 10, such as the gaze target $G_T$, the gaze direction $G_D$, a time period $t_{GE}$ of gaze engagement, or a collective time period $T_{GE}$ of gaze engagement. The time period $t_E$ of gaze engagement is the length of time the gaze target $G_T$ of the user 10 corresponds to a genre 26 of media content 20. The collective time period $T_E$ of gaze engagement is a summation of time periods $t_{GE}$ of gaze engagement of the user 10 while the user 10 is within the media content tracking environment 100. For example, the user 10 may stare at a display screen 122 (e.g., a first display screen 122a) with a genre 26 of media content 20 then transfer his or her gaze to a different display screen 122 (e.g., a second, third, fourth, fifth, sixth, seventh, or eighth display screen 122b-h) several times during a viewing session within the media content tracking environment 100.

Additionally or alternatively, when the media content tracking environment 100 has more than one user 10 (e.g., first, second, and third users 10a-c), the processing system 110 may determine gaze characteristics of a group 11 of more than one user 10. The gaze characteristics of the group 11 may be collective group gaze characteristics or gaze characteristics of a single user 10 with reference to the group of more than one user 10. For example, the processing system 110 determines collective group gaze characteristics similar to the gaze characteristics of the user 10, such as a group collective time period $T_{GE}$ of gaze engagement (i.e. a summation of the time period of gaze engagement of all users with reference to genre 26 of media content 20 or a particular display screen 122). In some implementations, the processing system 110 determines a concentration $C_E$ of collective gaze engagement. The concentration $C_E$ of collective gaze engagement is a ratio of the collective time period $T_E$ of gaze engagement and a total time (e.g., total time of a user 10 or total time of all users 10a-n) within the media content tracking environment 100. The ratio may be with reference to a particular display screen 122, a particular genre 26 of media content 20, a particular user 10 ($C_{E_{user}}$), or the group 11 of more than one user 10 ($C_{E_{group}}$). Examples of the ratio are shown below in equations 1 and 2.

$$C_{E_{user}} = \left(\frac{T_E}{\text{total time}_{user}}\right)_{display\ screen,\ genre} \quad (1)$$

$$C_{E_{group}} = \left(\frac{T_{GE}}{\text{total time}_{group}}\right)_{display\ screen,\ genre} \quad (2)$$

In some implementations, the processing system 110 stores the gaze characteristics as gaze characteristic data in the memory hardware 114. In some examples, the processing system 110 stores all generated gaze characteristics within the memory hardware 114. In other examples, an entity, such as an end-user, a processing system programmer, or a media content tracking environment provider, provides parameters that function as thresholds to store gaze characteristic data that qualifies according to the provided thresholds. The entity may consider gaze characteristic data stored according to thresholds more meaningful to review or to evaluate than all generated gaze characteristics. For example, thresholds permit the entity to efficiently and effectively evaluate media content 20 provided within the media content tracking environment 100. A media content provider may use the media content tracking environment 100 to evaluate whether one type of media content 20 more effectively engages users 10 than another type of media content 20. With thresholds, the entity can easily identify a level of gaze engagement that interests the entity. For example, the level of gaze engagement may be set according to thresholds such that the entity receives gaze characteristics corresponding to a level of gaze engagement greater than the thresholds. The processing system 110 may include default thresholds or receive thresholds from an entity. Some example thresholds that the processing system 110 may receive and/or identify include a threshold time number of gazes by at least one user 10, a threshold a collective time period $T_E$ of gaze engagement by the at least one user 10, a threshold concentration $C_E$ of collective gaze engagement by the at least one user 10, a threshold display time (i.e., a length of time provided media content 20 is displayed), or a threshold number of users 10.

Additionally or alternatively, the processing system 110 may store all gaze characteristics data or gaze characteristics data corresponding to thresholds in a gaze characteristic database. The gaze characteristic database maybe located within the memory hardware 114, on the network 116, or on the server 118. The characteristic database may be configured such that an entity may be able to filter gaze characteristics data according to filtering thresholds. For example, the filtering thresholds are values defined by the entity to remove or to hide gaze characteristics data such that the entity may review and may evaluate less gaze characteristic data than all gaze characteristic data or all gaze characteristics data corresponding to thresholds.

FIGS. 1A and 1B are examples of media content tracking environments 100 that include eight display systems 120, 120a-h with eight corresponding screens 122, 122a-h. Other arrangements are possible as well. With display systems 120, the media content tracking environment 100 may interpret the interest of the user 10 between display systems 120 via the gaze target of the user 10. In some implementations, while one display system 120 (e.g., a first display system 120a) displays media content 20 on a corresponding screen 122 (e.g., the first screen 122a), another display system 120 (e.g., an eighth display system 120h) away from the one display system 120, 120a displays the same media content 20 on a corresponding screen 122 (e.g., the eighth screen 122h). In these examples, the media content tracking environment 100 then determines whether the gaze characteristics of the user 10 indicate a change in the gaze target $G_T$ to the other display system 120 (e.g., from the first display system 120a to the eighth display system 120h). For example, the gaze target $G_T$ of the user 10 indicates a change when the gaze target $G_T$ transfers from the first display screen 122, 122a to the eighth display screen 122, 122h. The display systems 120 may also determine the interest of the user 10 for an interval of time t in relation to a genre 26 of media content 20. For example, at least two display systems 120 (e.g., the first and second display systems 120a-b) display on corresponding screens 122 (e.g., the first and second screens 122a-b) different genres 26 of media content 20 at the same interval of time t. The media content tracking environment 100 determines the gaze target $G_T$ of the user 10 according to the at least one image 310 from the imaging system 300. FIG. 1A and FIG. 1B are examples of media content tracking environments 100, except that FIG. 1A illustrates a single imaging system 300, while FIG. 1B illustrates a media content tracking environment 100 that uses multiple imaging systems 300, 300a-h. A reason the media content tracking environment 100 may be configured with different numbers of imaging systems 300 is that the media content tracking environment 100 may require greater tracking accuracy especially when the media content tracking environment 100 includes more than one user 10. Another reason is that the media content tracking environment 100 is a size that may cause a single imaging system 300 to be inaccurate due to a wide angle. Thus, the media content tracking environment 100 may include a number of imaging systems 300 to provide accurate tracking of gaze characteristics relative to the amount of users 10 within the media content tracking environment 100.

Figure 2:
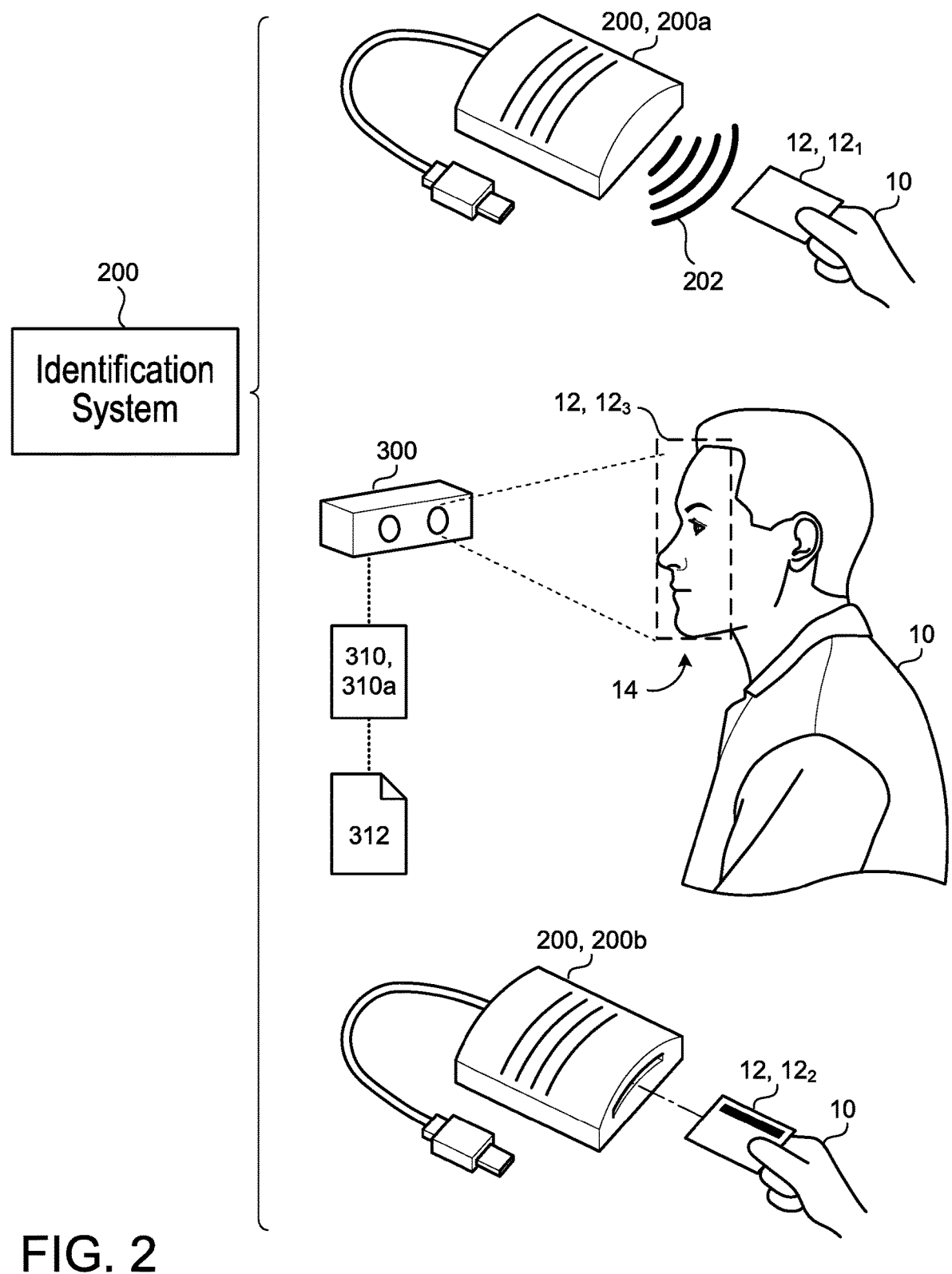
FIG. 2 is a schematic view of an example identification system within the media content tracking environment.

FIG. 2 illustrates example identification systems 200. Each identification system 200 receives the user identifier 12 associated with the user 10 and communicates user information included in the user identifier 12 to the processing system 110. The user information may range from basic user information to more complex user information that may influence media content preferences of the user 10. For example, basic user information includes at least one of a name, an age, a gender, or a sex of the user 10. Examples of more complex information include a property address, income, a size of property, a status of property (e.g., rental or own), a goods and/or services purchasing history, partisanships, or other information related to the user 10 that may influence media content preferences of the user 10.

Referring further to FIG. 2, some examples of user identifiers 12 are identification cards 12, $12_1$, $12_2$ or facial recognition 12, $12_3$. For example, a first identification card $12_1$ is a near field communication card embedded with a near field communication chip configured to communicate with another near field communication chip when in close proximity. In some examples, the first identification card 12, $12_1$ communicates with an electromagnetic near field scanner 200, 200a by a near field measurement 202 of electromagnetic induction as the first identification card 12, $12_1$ moves through a magnetic field associated with the near field scanner 200, 200a. When the first identification card 12, $12_1$ is in close proximity with the electromagnetic near field scanner 200, 200a, the electromagnetic near field scanner 200, 200a is configured to read user information from the first identification card 12, $12_1$. In some implementations, a second identification card 12, $12_2$ is a swipe card with a magnetic strip to identify the user 10 and/or transfer user information. The second identification card 12, $12_2$ may be preprogrammed with user information in the magnetic strip such that when the user 10 swipes the second identification card 12, $12_3$, a magnetic card reader 200, 200b receives the user information from the magnetic strip.

Additionally or alternatively, an imaging system 300 performs facial recognition 12, $12_3$ as the user identifier 12. The imaging system 300 may be the same imaging system 300 used to determine the gaze target $G_T$ of the user 10 or a dedicated imaging system 300, 300a for facial recognition 12, $12_3$. The imaging system 300 performs facial recognition 12, $12_3$ based on facial features 14 of the user 10. To perform facial recognition 12, $12_3$, the imaging system 300 captures at least one facial recognition image 310, 310a, generates corresponding image data 312, and communicates the image data 312 to the processing system 110. The processing system 110 is configured to identify and determine the user identifier 12 from the image data 312 based on facial features 14 of the user 10 captured by the at least one facial recognition image 310, 310a. In some examples, the processing system 110 communicates with a facial recognition database that compares image data 312 from the facial recognition database to image data 312 communicated to the processing system 110 from the imaging system 300. Generally, image data 312 for facial recognition 12, $12_3$ corresponds to several nodal points related to facial features 14 of a user 10, such as peaks and valleys around a mouth, a nose, eyes, a chin, a jawline, a hairline, etc. The processing system 110 may include facial recognition software to perform facial recognition 12, $12_3$.

In some examples, the identification system 200 automatically launches media content 20. For example, the user identifier 12 (e.g., 12, $12_{1-3}$) of the user 10 includes user information corresponding to a genre 26 of media content 20 related to the user 10. When the identification system 200 identifies the user identifier 12 (e.g., by identification card 12, $12_{1,2}$ or facial recognition 12, $12_3$), the identification system 200 communicates uniform resource locators (URLs) within the user information to the processing system 110 such that the processing system 110 instructs the display system 120 to display a genre 26 of media content 20 related to the user 10 based on the URLs within the user identifier 12.

Figure 3:
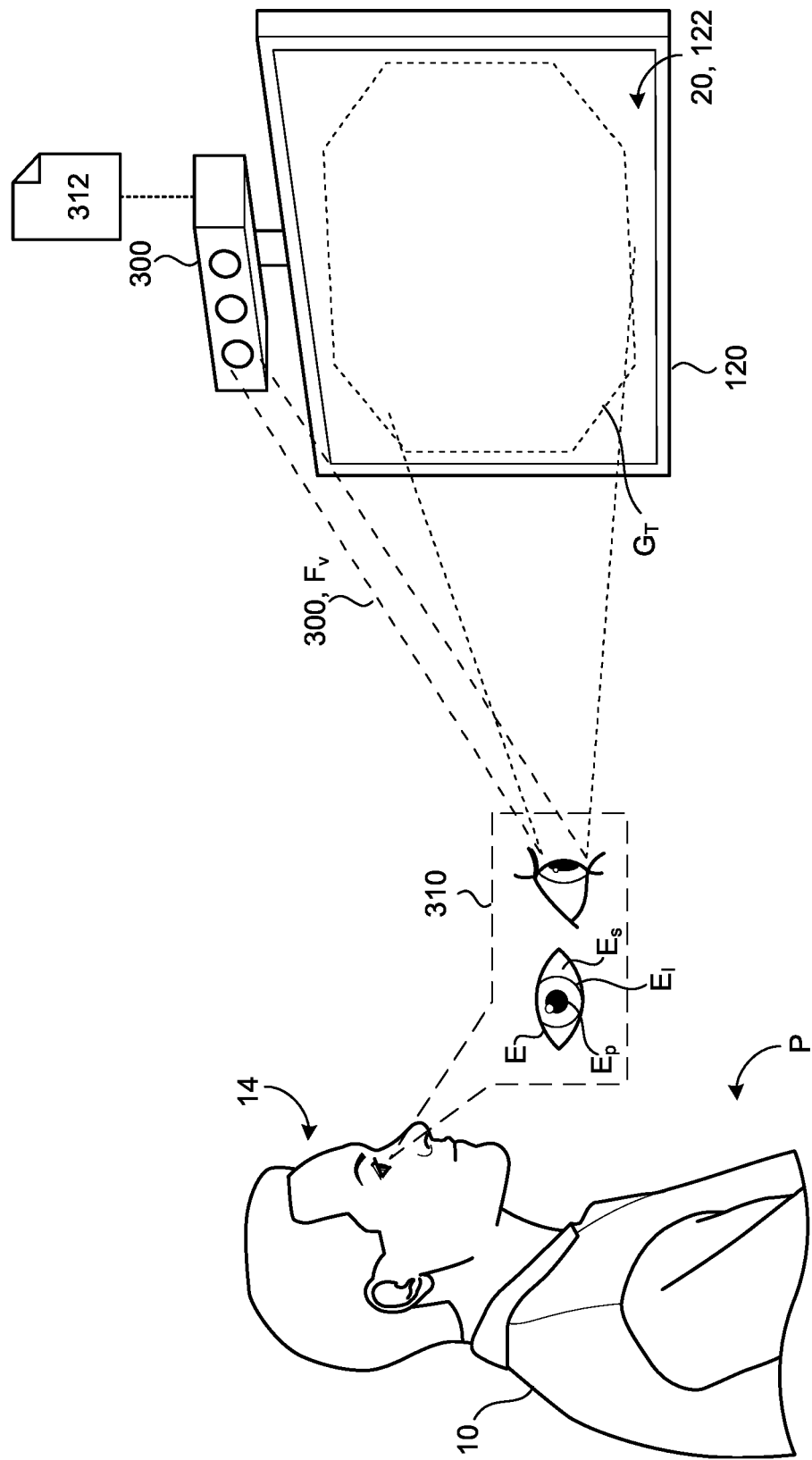
FIG. 3 is a schematic view of an example imaging system in the media content tracking environment.

FIG. 3 provides an example of the imaging system 300. The imaging system 300 is arranged with a field of view $F_v$ to capture at least a portion of the media content tracking environment 100 such that the imaging system 300 captures at least one user 10. To capture at least one user 10, the imaging system 300 may be a camera (e.g., video camera, still camera, or stereo camera) or a sensor or a combination of both a camera and a sensor. In some examples, the sensor is a three-dimension volumetric point cloud imaging sensor (e.g., 3D scanner) that collects image data 312 regarding surfaces within a field of view $F_v$. Additionally or alternatively, the imaging system 300 may be a light detection and ranging (LIDAR) system or a laser detection and ranging (LADAR) system that uses a light or a laser to determine a distance from the imaging system 300 according to time of flight of the light or the laser. The imaging system 300 captures at least one image 310, and from the at least one image 310, the processing system 110 may determine the gaze target $G_T$ of the user 10. To determine the gaze target $G_T$ of the user 10, the imaging system 300 communicates the at least one image 310 as image data to the processing system 110. In some examples, the at least one image 310 includes at least one facial feature 14 (e.g., eye, ear, nose, chin, mouth, jawline, hairline, etc.) of the user 10. When the imaging system 300 captures at least one image 310 of the at least one facial feature 14, the imaging system 300 generates image data 312 corresponding to aspects of the at least one facial feature 14, such as curvature, peaks, valleys, such that the image data may be a topographic spatial map of the facial feature 14. In some examples, the image data 312 is three-dimensional depth coordinates relative to a position of the imaging system 300. Once the imaging system 300 communicates the image data to the processing system 110, the processing system 110 determines gaze characteristics of the user 10 or users 10 based on the image data.

FIG. 3 illustrates the at least one image 310 includes at least one eye E of the user 10. With at least one image 310 of the at least one eye E of the user 10, the imaging system 300 generates image data 312 corresponding to a spherical curvature of the eye E (e.g., the cornea of the eye E including the pupil, the sclera, and the iris). The processing system 110 may determine the spherical curvature of the eye E with respect to other facial features 14 (e.g., ear, nose, chin, mouth, jawline, hairline, etc.) or physical features (e.g., shoulders, torso, etc.) regarding a posture P of the user 10 captured by the image data 312 from the at least one image 310. With the spherical curvature of the eye E, the processing system 110 may determine the gaze direction $G_D$ and the gaze target $G_T$. For example, the processing system 110 approximates a center point of the eye E corresponding to the pupil $E_p$ of the eye E.

Additionally or alternatively, the media content tracking environment 100 includes a calibration process. During the calibration process, a user 10 follows a sequence of gaze targets $G_T$ displayed on different screens 122 with the display systems 120 of the media content tracking environment 100. With the sequence preprogrammed, the processing system 110 stores image data from the calibration corresponding to each gaze target $G_T$ within the sequence to associate with image data generated after calibration when the user 10 receives non-calibration media content 20. From the association, the processing system 110 may more accurately determine gaze characteristics of the user 10.

Figure 4A:
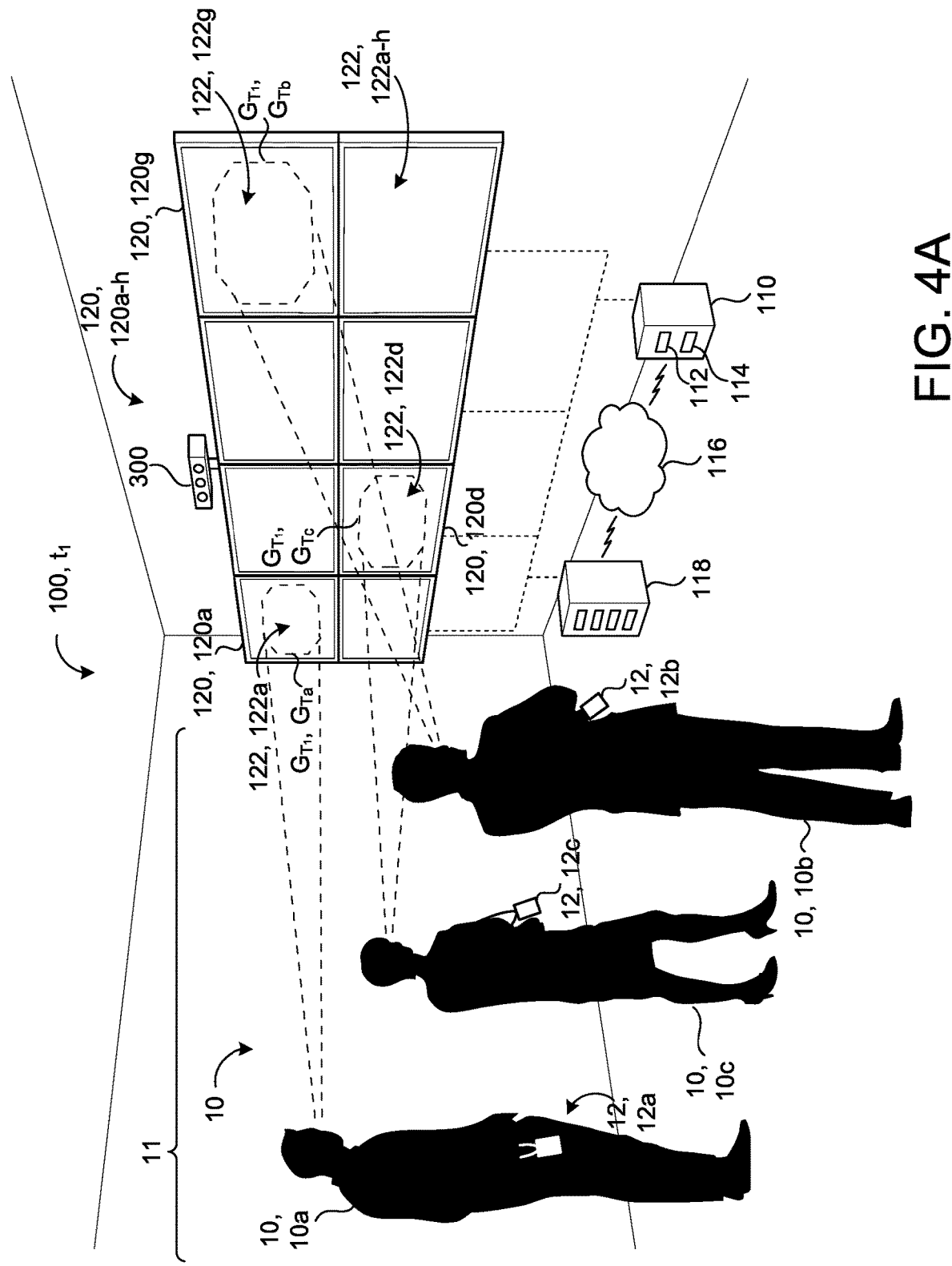
FIG. 4A is a schematic view of an example media content tracking environment at a first interval of time.
Figure 4B:
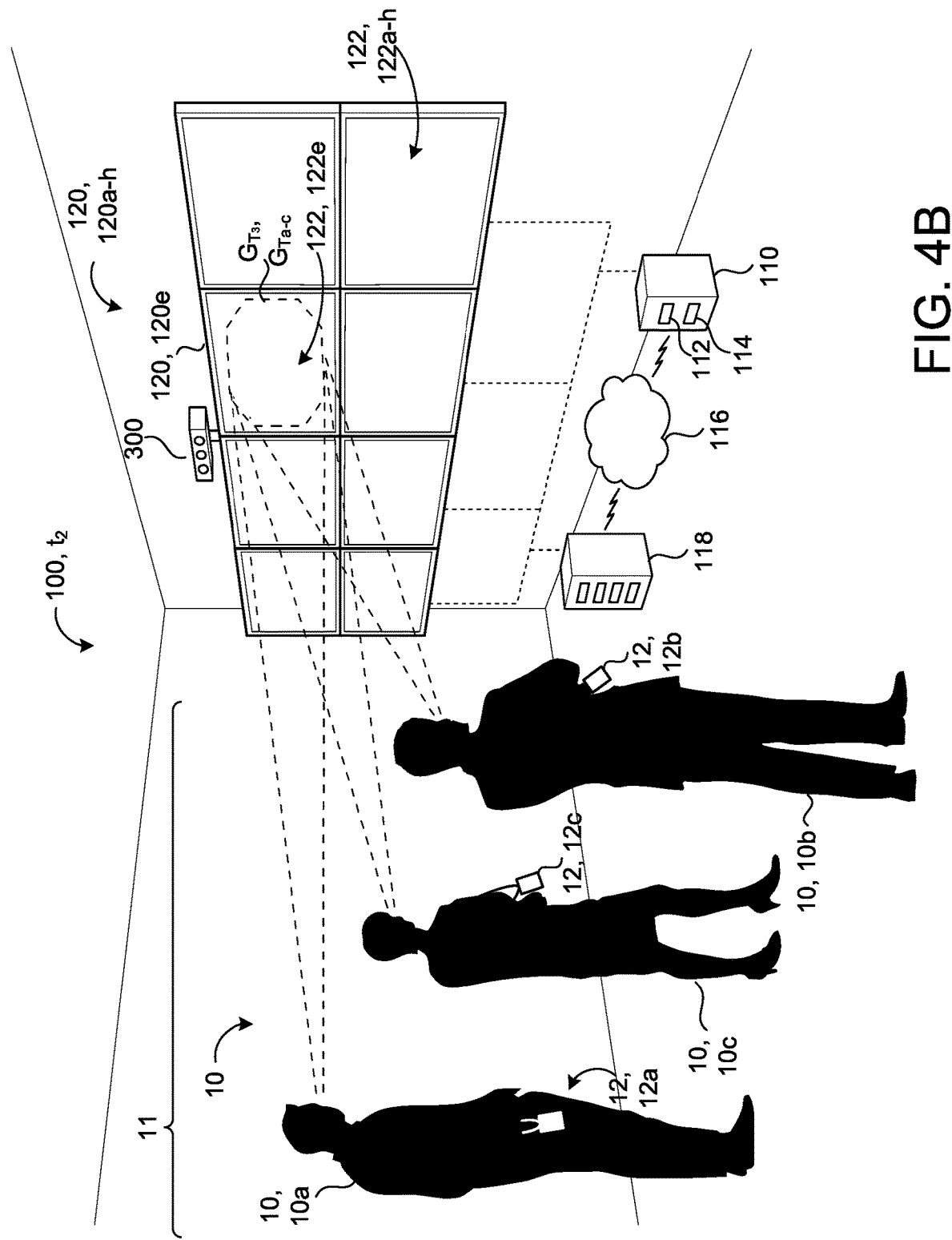
FIG. 4B is a schematic view of the media content tracking environment at a second interval of time.

FIGS. 4A-4C provide examples of a media content tracking environment 100 over a period of time t. FIGS. 4A-4C include three users 10, 10a-c with corresponding user identifiers 12, 12a-c. The media content tracking environment 100, like FIGS. 1A-1B, includes eight display systems 120, 120a-h with eight corresponding screens 122, 122a-h and one imaging system 300. The media content tracking environment 100 of FIGS. 4A-4C also includes a processing system 110, a network 116, and a server 118.

FIG. 4A illustrates an example of the media content tracking environment 100 at a first interval of time $t_1$ within the period of time t. At this first interval of time $t_1$, the user 10, 10a has a gaze target $G_{T1}$, $G_{Ta}$ corresponding to display screen 122, 122a such that the media content 20 depicted on the display screen 122, 122a consumes an attention of user 10, 10a. Similarly, the media content 20 depicted on the display screen 122, 122g attracts an attention of user 10, 10b such that at this first interval of time $t_1$, user 10, 10b has a gaze target $G_{T1}$, $G_{Tb}$ corresponding to display screen 122, 122g of display system 120, 120g. At the first interval of time $t_1$, user 10, 10c has a gaze target $G_{T1}$, $G_{Tc}$ corresponding to display screen 122, 122d of display system 120, 120d.

FIG. 4B illustrates an example of the media content tracking environment 100 at a second interval of time $t_2$ within the period of time t. At this interval of time $t_2$, each user 10, 10a-c has had a change of attention from gaze target $G_{T1}$ of the first interval of time $t_1$ to gaze target $G_{T2}$ of the second interval of time $t_2$. As illustrated by FIG. 4B, each user 10, 10a-c, at the second interval of time $t_2$ has a gaze target $G_{T2}$, $G_{Ta-c}$ corresponding to display screen 122, 122e of display system 120, 120e. Each user 10, 10a-c may have changed his or her gaze target $G_{T1}$ either because the display screen 122 corresponding to his or her gaze target $G_{T1}$ changed media content 20 or display screen 122, 122e changed to more interesting media content 20, $t_2$. For example, the more interesting media content 20, $t_2$ is a different genre 26 of media content 20.

FIG. 4C illustrates an example of the media content tracking environment 100 at a third interval of time $t_3$ within the period of time t. At this third interval of time $t_3$, the processing system 110 has changed the media content 20 corresponding to display screen 122, 122e such that each user 10, 10a-c has a different gaze target $G_{T3}$ at the third interval of time $t_3$ than the gaze target $G_{T2}$ at the second interval of time $t_2$. At this third interval of time $t_3$, the gaze target $G_{T3}$, $G_{Ta}$ of user 10, 10a is the media content 20 of display screen 122, 122c and the gaze target $G_{T3}$, $G_{Tb-c}$ of user 10, 10b-c is the media content 20 of display screen 122, 122f.

Figure 5A:
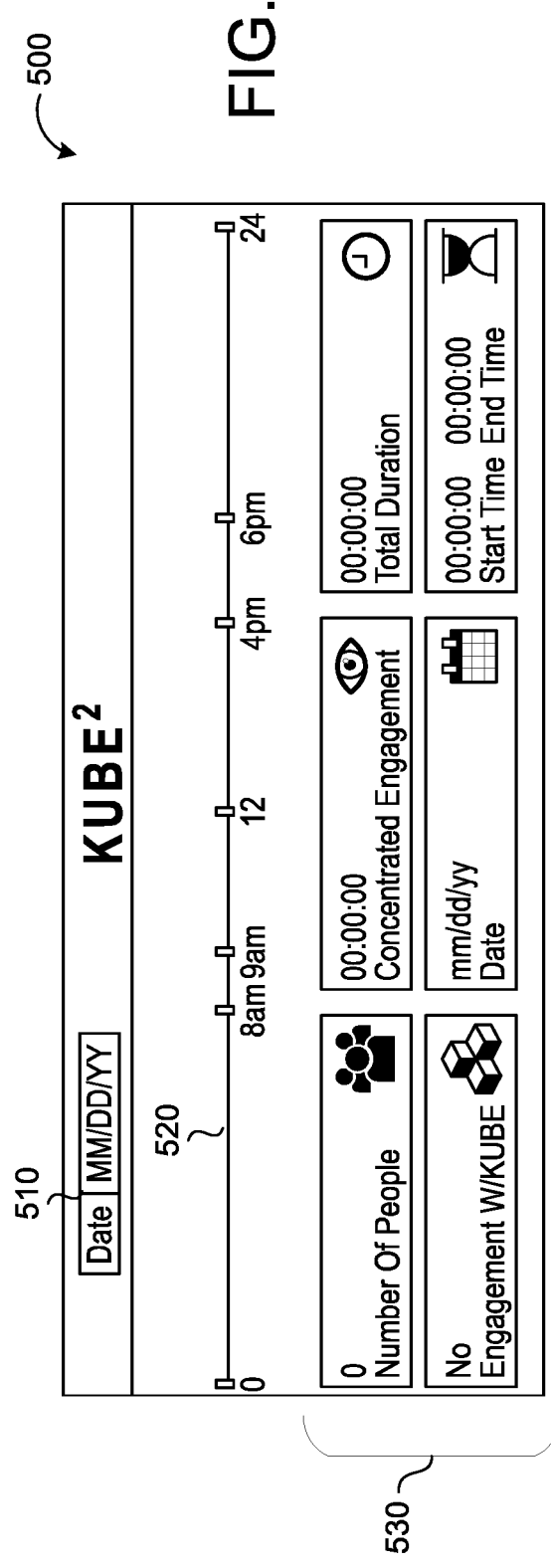
FIGS. 5A and 5B are schematic views of example dashboard views of a graphical user interface for a media content tracking environment.
Figure 5B:
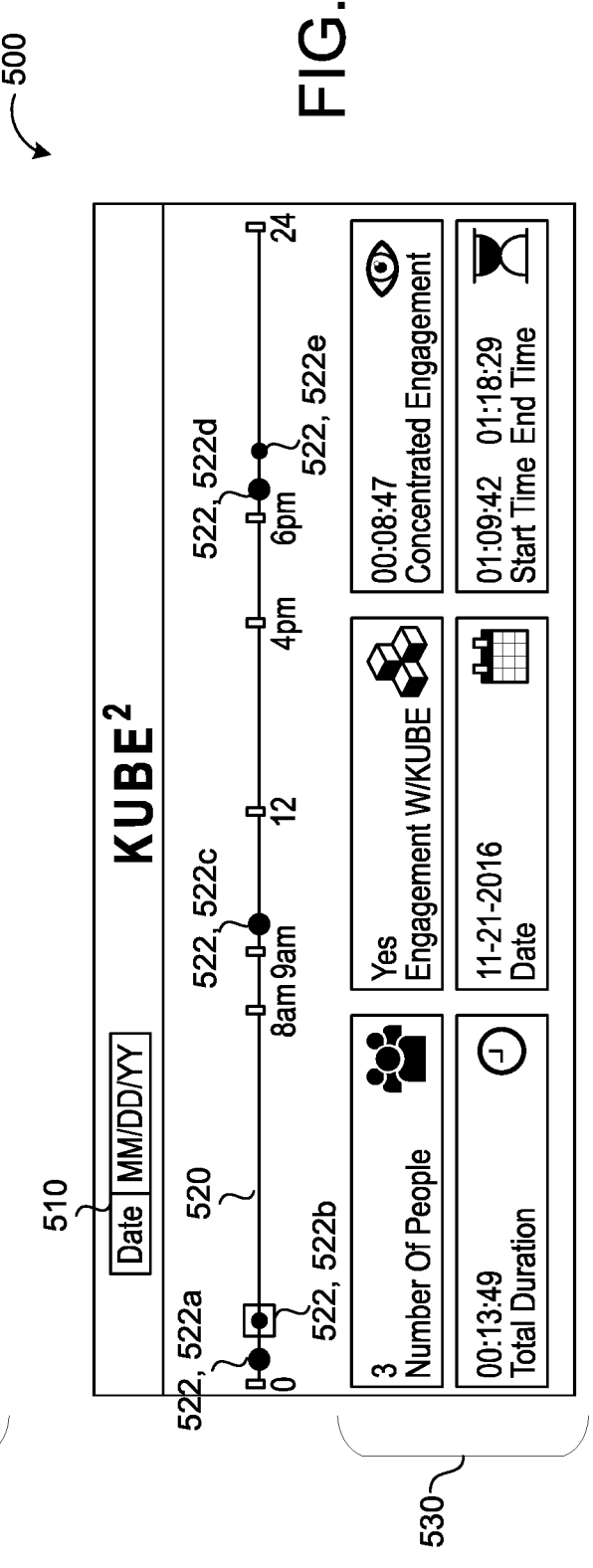

FIGS. 5A-5B provide example dashboard views of a user interface 500 output by the processing system 110. The user interface 500 is configured to display gaze characteristics corresponding to a viewing session by at least one user 10. In some implementations, the user interface 500 includes details regarding media content 20 that interested at least one user 10 during the viewing session. FIG. 5A is an example template of the user interface 500 before either the processing system 110, the network 116, or the server 118 link media content tracking environment data to the user interface 500. FIG. 5B is an example of the user interface 500 after the user interface 500 has been linked to the media content tracking environment data. FIG. 5B illustrates that the entity selected 11-21-2016 as the date from the date selector 510 and data point 522, 522b from the timeline 520.

FIGS. 5A and 5B illustrate an example user interface 500 that includes a date selector 510 selectable by an entity. Upon selection of a date, the user interface 500 is configured to display a timeline 520 corresponding to a viewing session of at least one user 10 from the date selected by the entity. If the entity selects a data point 522 from the timeline 520, the user interface 500 displays session characteristics 530, such as number of people 532, whether engagement occurred during the session, a start time of engagement, a stop time of engagement, and/or a total duration of engagement. In some implementations, the user interface 500 displays gaze characteristics corresponding to the data point 522 selected by the entity from the timeline 520.

Figure 6:
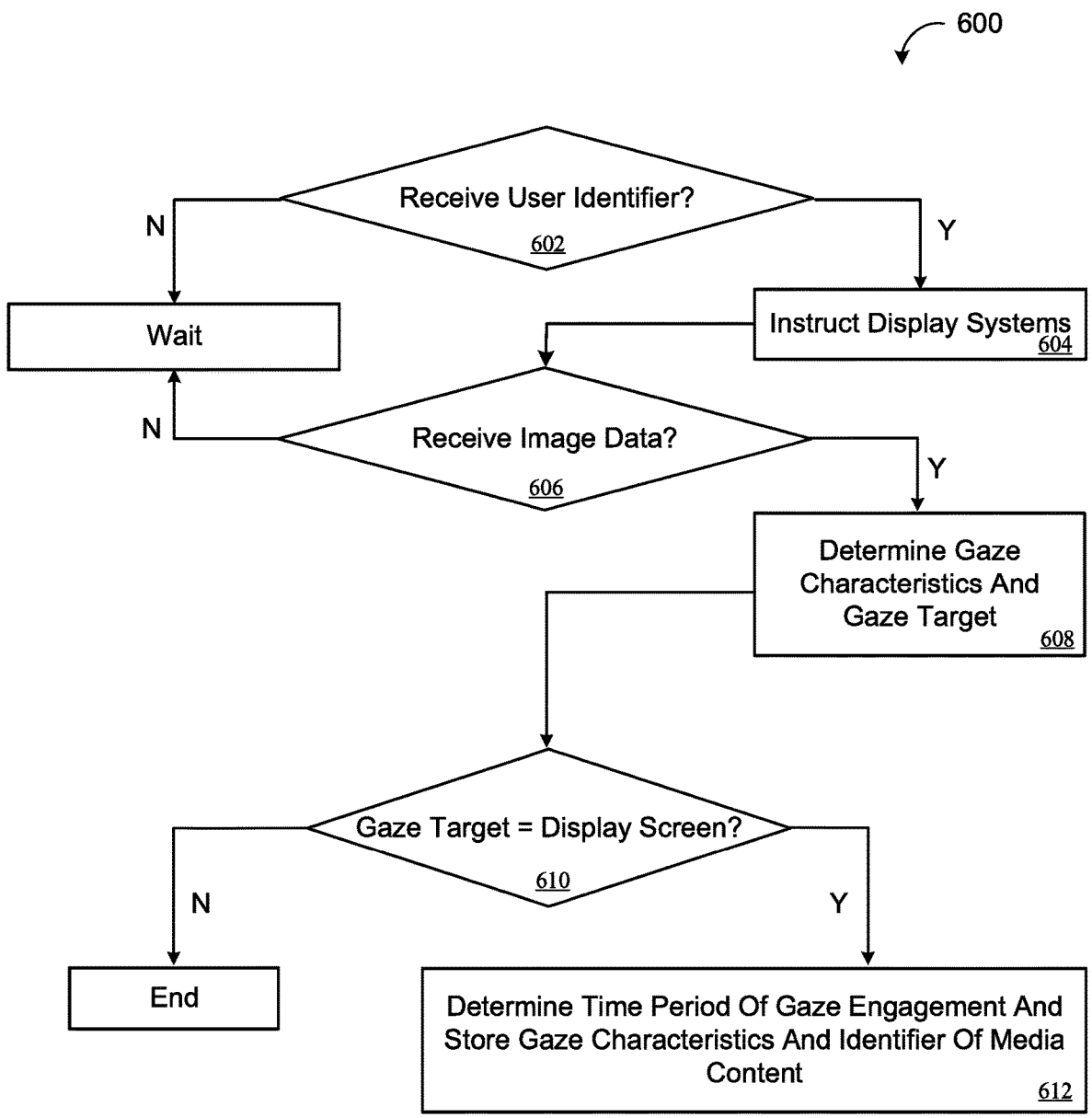
FIG. 6 is an example flow diagram of operations of a method of tracking audience engagement of various media content.

FIG. 6 is an example arrangement of operations for a method 600 of media content tracking. At operation 602, the method 600 includes receiving a user identifier 12 associated with a user 10. In some implementations, the method 600 may receive user identifiers 12 associated with a plurality of users 10. The method 600 further includes, at operation 604, instructing display systems 120 to display media content 20 based on the user identifier 12. Each display system 120 includes a corresponding screen 122. When, at operation 606, the processing system 110 receives image data from an imaging system 300 configured to have a field of view $F_V$ arranged to capture images 310 of the user 10, the method 600 proceeds to operation 608. Otherwise, the processing system 110 waits for image data from the imaging system 300.

At operation 608, the method 600 includes determining gaze characteristics of the user 10 based on the image data. At operation 608, the method 600 further includes determining gaze characteristics including a gaze target $G_T$ of the user 10. In some examples, the method 600 also includes determining a gaze direction $G_D$ of the user 10. The method 600 further includes, at operation 610, determining whether the gaze target $G_T$ corresponds to one of the screens 122. When the gaze target corresponds to one of the screens 122, the method 600 proceeds to operation 612. Otherwise, when the gaze target does not correspond to one of the screens 122, the method 600 may end operations. At operation 612, the method 600 includes determining a time period of gaze engagement with the corresponding screen 122 based on the gaze characteristics of the user 10. At operation 612, the method 600 further includes storing at least one of the gaze characteristics of the user or the time period t of gaze engagement with the corresponding screen 122 and the media content 20 or an identifier 22 of the media content 20 displayed on the screen 122 corresponding to the gaze target $G_T$. Additionally or alternatively, the method 600 may further include identifying genres 26 of media content 20 receiving gaze engagement by the users 10 based on the associations of the time periods of gaze engagement of the users 10 with the corresponding media content 20. Optionally, the method 600 may include storing the identified genres 26 of media content 20.

Figure 7:
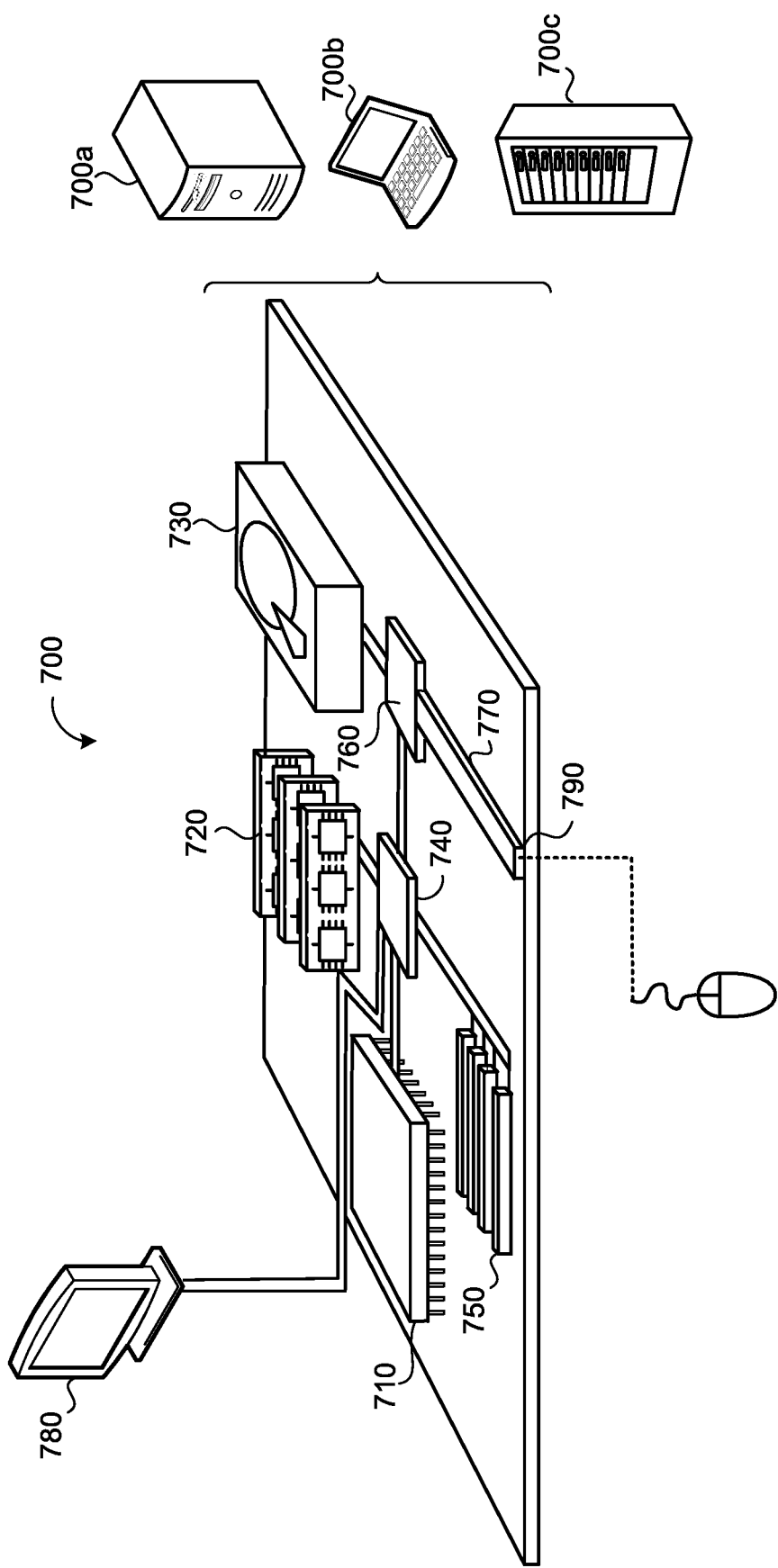
FIG. 7 is a schematic view of an example computing device that may be used to implement the systems and methods described herein.

FIG. 7 is schematic view of an example computing device 700 that may be used to implement the systems and methods described in this document. The computing device 700 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations of the inventions described and/or claimed in this document.

The computing device 700 includes a processor 710, memory 720, a storage device 730, a high-speed interface/controller 740 connecting to the memory 720 and high-speed expansion ports 750, and a low speed interface/controller 760 connecting to a low speed bus 770 and a storage device 730. Each of the components 710, 720, 730, 740, 750, and 760, are interconnected using various busses, and may be mounted on a common motherboard or in other manners as appropriate. The processor 710 can process instructions for execution within the computing device 700, including instructions stored in the memory 720 or on the storage device 730 to display graphical information for a graphical user interface (GUI) on an external input/output device, such as display 780 coupled to high speed interface 740. In other implementations, multiple processors and/or multiple buses may be used, as appropriate, along with multiple memories and types of memory. Also, multiple computing devices 700 may be connected, with each device providing portions of the necessary operations (e.g., as a server bank, a group of blade servers, or a multi-processor system).

The memory 720 stores information non-transitorily within the computing device 700. The memory 720 may be a computer-readable medium, a volatile memory unit(s), or non-volatile memory unit(s). The non-transitory memory 720 may be physical devices used to store programs (e.g., sequences of instructions) or data (e.g., program state information) on a temporary or permanent basis for use by the computing device 700. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

The storage device 730 is capable of providing mass storage for the computing device 700. In some implementations, the storage device 730 is a computer-readable medium. In various different implementations, the storage device 730 may be a floppy disk device, a hard disk device, an optical disk device, or a tape device, a flash memory or other similar solid state memory device, or an array of devices, including devices in a storage area network or other configurations. In additional implementations, a computer program product is tangibly embodied in an information carrier. The computer program product contains instructions that, when executed, perform one or more methods, such as those described above. The information carrier is a computer- or machine-readable medium, such as the memory 720, the storage device 730, or memory on processor 710.

The high speed controller 740 manages bandwidth-intensive operations for the computing device 700, while the low speed controller 760 manages lower bandwidth-intensive operations. Such allocation of duties is exemplary only. In some implementations, the high-speed controller 740 is coupled to the memory 720, the display 780 (e.g., through a graphics processor or accelerator), and to the high-speed expansion ports 750, which may accept various expansion cards (not shown). In some implementations, the low-speed controller 760 is coupled to the storage device 730 and a low-speed expansion port 790. The low-speed expansion port 790, which may include various communication ports (e.g., USB, Bluetooth, Ethernet, wireless Ethernet), may be coupled to one or more input/output devices, such as a keyboard, a pointing device, a scanner, or a networking device such as a switch or router, e.g., through a network adapter.

The computing device 700 may be implemented in a number of different forms, as shown in the figure. For example, it may be implemented as a standard server 700a or multiple times in a group of such servers 700a, as a laptop computer 700b, or as part of a rack server system 700c.

Various implementations of the systems and techniques described herein can be realized in digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The processes and logic flows described in this specification can be performed by one or more programmable processors executing one or more computer programs to perform functions by operating on input data and generating output. The processes and logic flows can also be performed by special purpose logic circuitry, e.g., an FPGA (field programmable gate array) or an ASIC (application specific integrated circuit). Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A number of implementations have been described. Nevertheless, it will be understood that various modifications may be made without departing from the spirit and scope of the disclosure. Accordingly, other implementations are within the scope of the following claims.

What is claimed is:

1. A method comprising:
receiving, at data processing hardware, a user identifier associated with a user, the user identifier associated with the user comprising uniform resource locaters (URLs) indicating a first genre of media content relating to the user;
instructing, by the data processing hardware, each of a plurality of display systems to concurrently display a respective genre of media content with a first display system of the plurality of display systems displaying the first genre of media content relating to the user based on the URLs associated with the received user identifier and a second display system of the plurality of display systems displaying a second genre of media content different than the first genre of media content, each of the plurality of display systems having a corresponding screen arranged about the user, and each of the screens concurrently viewable by the user;
receiving, at the data processing hardware, image data from an imaging system configured to have a field of view arranged to capture images of the user while the user views the corresponding screens of the plurality of display systems;
determining, by the data processing hardware, gaze characteristics of the user based on the image data, the gaze characteristics comprising a gaze target of the user;
determining, by the data processing hardware, whether the gaze target corresponds to one of the screens; and
when the gaze target corresponds to the corresponding screen of the first display system:
determining, by the data processing hardware, a time period of gaze engagement with the corresponding screen of the first display system based on the gaze characteristics of the user; and
storing, by the data processing hardware, in memory hardware, gaze-characteristic data comprising:
at least one of the gaze characteristics of the user or the time period of gaze engagement with the corresponding screen of the first display system; and
the media content or an identifier of the media content displayed on the corresponding screen of the first display system.

2. The method of claim 1, further comprising, when the gaze target corresponds to the corresponding screen of the first display system:
instructing, by the data processing hardware, one of the plurality of display systems to display on the corresponding screen of another display system away from the gaze target the first genre of media content displayed on the corresponding screen of the first display system; and
determining, by the data processing hardware, whether the gaze characteristics of the user indicate a change in the gaze target to the corresponding screen of the other display system.

3. The method of claim 1, wherein determining the gaze characteristics of the user comprises determining a gaze direction of the user and the gaze target of the user based on the gaze direction of the user.

4. The method of claim 1, further comprising, for the second genre of media content, determining, by the data processing hardware, a collective time period of gaze engagement by the user in the second genre of media content based on any time periods of gaze engagement of the user with the second genre of media content.

5. The method of claim 1, further comprising identifying, by the data processing hardware, which of the first genre of media content and the second genre of media content having received at least one of:
- a threshold number of gazes by the user; or
- a threshold collective time period of gaze engagement by the user.

6. The method of claim 1, further comprising determining, by the data processing hardware, the user identifier based on the image data.

7. The method of claim 6, further comprising:
- identifying, by the data processing hardware, facial features of the user identifier based on the image data; and
- determining, by the data processing hardware, the user identifier based on the facial features of the user.

8. The method of claim 1, wherein the imaging system comprises at least one of:
- a camera;
- a three-dimension volumetric point cloud imaging sensor;
- stereo cameras;
- a light detection and ranging (LIDAR) system; or
- a laser detection and ranging (LADAR) system.

9. The method of claim 1, wherein receiving the user identifier comprises receiving a near-field measurement from an electro-magnetic near-field scanner.

10. The method of claim 1, further comprising executing a calibration comprising
- displaying, by the data processing hardware, a sequence of calibration gaze targets on the corresponding screens of the plurality of display systems;
- receiving, at the data processing hardware, from the imaging system, calibration image data corresponding to each calibration gaze target; and
- storing, by the data processing hardware, in the memory hardware, the calibration image data corresponding to each calibration gaze target.

11. The method of claim 10, wherein determining the gaze characteristics of the user comprises:
- retrieving, by the data processing hardware, from the memory hardware, the calibration image data corresponding to each calibration gaze target; and
- comparing, by the data processing hardware, the image data with the retrieved calibration image data to determine an association between the image data and the calibration gaze target corresponding to the retrieved calibration image data.

12. The method of claim 1, wherein the user identifier comprises user information, and wherein the first genre of media content relating to the user is based on the user information.

13. The method of claim 12, wherein the user information comprises at least one of a name, an age, a gender, a property address, a property size, a property status, an income, a purchasing history, or a partisanship.

14. The method of claim 1, further comprising:
- determining, by the data processing hardware, whether the gaze characteristics satisfy a gaze-characteristic threshold; and
- when the gaze characteristics fail to satisfy the gaze-characteristic threshold, not storing the gaze-characteristic data.

15. The method of claim 14, wherein the gaze-characteristic threshold comprises at least one of a threshold number of gazes by the user, a threshold a collective time period of gaze engagement by the user, or a threshold concentration of collective gaze engagement by the user.

16. A system comprising:
- data processing hardware in communication with a plurality of display systems; and
- memory hardware in communication with the data processing hardware, the memory hardware storing instructions that when executed on the data processing hardware cause the data processing hardware to perform operations comprising:
  - receiving a user identifier associated with a user, the user identifier associated with the user comprising uniform resource locaters (URLs) indicating a first genre of media content relating to the user;
  - instructing each of the plurality of display systems to concurrently display a respective genre of media content with a first display system of the plurality of display systems displaying the first genre of media content relating to the user based on the URLs associated with the received user identifier and a second display system of the plurality of display systems displaying a second genre of media content different than the first genre of media content, each of the plurality of display systems having a corresponding screen arranged about the user, and each of the screens concurrently viewable by the user;
  - receiving image data from an imaging system configured to have a field of view arranged to capture images of the user while the user views the corresponding screens of the plurality of display systems;
  - determining gaze characteristics of the user based on the image data, the gaze characteristics comprising a gaze target of the user;
  - determining whether the gaze target corresponds to one of the screens; and
  - when the gaze target corresponds to the corresponding screen of the first display system:
    - determining a time period of gaze engagement with the corresponding screen of the first display system based on the gaze characteristics of the user; and
    - storing, in the memory hardware, gaze-characteristic data comprising:
      - at least one of the gaze characteristics of the user or the time period of gaze engagement with the corresponding screen of the first display system; and
      - the media content or an identifier of the media content displayed on the corresponding screen of the first display system.

17. The system of claim 16, wherein the operations further comprise, when the gaze target corresponds to the corresponding screen of the first display system:
- instructing one of the plurality of display systems to display on the corresponding screen of another display system away from the gaze target the first genre of media content displayed on the corresponding screen of the first display system; and
- determining whether the gaze characteristics of the user indicate a change in the gaze target to the corresponding screen of the other display system.

18. The system of claim 16, wherein determining the gaze characteristics of the user comprises determining a gaze direction of the user and the gaze target of the user based on the gaze direction of the user.

19. The system of claim 16, wherein the operations further comprise, for the second genre of media content, determining a collective time period of gaze engagement by the user in the second genre of media content based on any time periods of gaze engagement of the user with the second genre of media content.

20. The system of claim 16, wherein the operations further comprise identifying which of the first genre of media content and the second genre of media content having received at least one of:
    a threshold number of gazes by the user; or
    a threshold collective time period of gaze engagement by the user.

21. The system of claim 16, wherein the operations further comprise determining the user identifier based on the image data.

22. The system of claim 21, wherein the operations further comprise:
    identifying facial features of the user identifier based on the image data; and
    determining the user identifier based on the facial features of the user.

23. The system of claim 16, wherein the imaging system comprises at least one of:
    a camera;
    a three-dimension volumetric point cloud imaging sensor;
    stereo cameras;
    a light detection and ranging (LIDAR) system; or
    a laser detection and ranging (LADAR) system.

24. The system of claim 16, wherein receiving the user identifier comprises receiving a near-field measurement from an electro-magnetic near-field scanner.

25. The system of claim 16, wherein the operations further comprise executing a calibration comprising:
    displaying a sequence of calibration gaze targets on screens of the plurality of display systems;
    receiving from the imaging system calibration image data corresponding to each calibration gaze target; and
    storing in the memory hardware the calibration image data corresponding to each calibration gaze target.

26. The system of claim 25, wherein determining the gaze characteristics of the user comprises:
    retrieving, from the memory hardware, the calibration image data corresponding to each calibration gaze target; and
    comparing the image data with the retrieved calibration image data to determine an association between the image data and the calibration gaze target corresponding to the retrieved calibration image data.

27. The system of claim 16, wherein the user identifier comprises user information, and wherein the first genre of media content relating to the user is based on the user information.

28. The system of claim 27, wherein the user information comprises at least one of a name, an age, a gender, a property address, a property size, a property status, an income, a purchasing history, or a partisanship.

29. The system of claim 16, wherein the operations further comprise:
    determining whether the gaze characteristics satisfy a gaze-characteristic threshold; and
    when the gaze characteristics fail to satisfy the gaze-characteristic threshold, not storing the gaze-characteristic data.

30. The system of claim 29, wherein the gaze-characteristic threshold comprises at least one of a threshold number of gazes by the user, a threshold a collective time period of gaze engagement by the user, or a threshold concentration of collective gaze engagement by the user.

* * * * *